United States Patent [19]
Rodriguez et al.

[11] Patent Number: 5,421,349
[45] Date of Patent: Jun. 6, 1995

[54] ATRAUMATIC PROXIMAL GUIDEWIRE END

[75] Inventors: Oscar E. Rodriguez, Miami; Robert P. Letendre, North Miami, both of Fla.

[73] Assignee: Cordis Corporation, Miami Lakes, Fla.

[21] Appl. No.: 261,334

[22] Filed: Jun. 16, 1994

[51] Int. Cl.⁶ ............................................. A61M 25/00
[52] U.S. Cl. .................................. 128/772; 128/657; 604/282
[58] Field of Search ............... 128/657, 772; 604/93, 604/95, 164, 166, 170, 280, 282

[56] References Cited

U.S. PATENT DOCUMENTS

| | | |
|---|---|---|
| 4,003,369 | 1/1977 | Heilman et al. ............... 128/772 |
| 4,721,117 | 1/1988 | Mar et al. . |
| 4,763,647 | 8/1988 | Gambale . |
| 4,846,186 | 7/1989 | Box et al. . |
| 4,846,193 | 7/1989 | Tremulis et al. ............... 128/772 |
| 4,867,173 | 9/1989 | Leoni . |
| 4,921,483 | 5/1990 | Wijay et al. . |
| 4,991,602 | 2/1991 | Amplatz et al. . |
| 5,120,308 | 6/1992 | Hess . |
| 5,147,317 | 9/1992 | Shank et al. ............... 128/657 X |
| 5,197,486 | 3/1993 | Frassica ............... 128/657 X |
| 5,209,735 | 5/1993 | Lazarus . |
| 5,243,996 | 9/1993 | Hall . |
| 5,247,942 | 9/1993 | Prather et al. . |
| 5,282,478 | 2/1994 | Fleischhacuer et al. ........... 128/772 |

*Primary Examiner*—Sam Rimell
*Attorney, Agent, or Firm*—Gerstman, Ellis & McMillin

[57] ABSTRACT

A vascular catheter guidewire comprises a length of wire having a proximal end, a distal end, and a central portion between the ends having a first diameter range. Typically the range of first diameters is quite narrow and within the dimensions of 0.01 and 0.02 inch. Both the distal end and the proximal end of the guidewire catheter each comprise a tip of greater flexibility than the wire of the central portion of the guidewire. The distal end tip and the proximal end tip are each defined by a length of wire which is integral with the central portion of wire and each has a range of diameters that is less than the range of first diameters. Typically, the diameters of the tip portion wires are on the order of 0.006 to 0.008 inch. The proximal end tip is significantly shorter than the distal end tip. The distal end tip is typically of greater flexibility than the proximal end tip. The proximal end tip is used to provide a blunt, flexible tip that does not tear rubber gloves or injure the fingers as the guidewire is manipulated from the proximal end. Nevertheless, because the proximal end tip is stiffer than the distal end tip, it is more capable of supporting a push of the guidewire, without tearing the rubber gloves for desired medical purposes, and it may be used with a torquing device.

14 Claims, 1 Drawing Sheet

ATRAUMATIC PROXIMAL GUIDEWIRE END

BACKGROUND OF THE INVENTION

Guidewires for vascular catheters are commonly used in angioplasty procedures relating to the coronary arteries and elsewhere. An example of such a guidewire is illustrated by Box U.S. Pat. No. 4,846,186. There, it is shown that the distal end of the guidewire carries a coil spring which may be nine or ten inches long as specifically described in the Box patent. Within the coil spring, the guidewire is tapered down to a relatively narrow width. A distal tip portion is attached by brazing to the end of the narrow-diameter distal guidewire section, which tip retains the distal end of the spring.

It is conventional for the proximal end of the guidewire to simply terminate with a flat end.

Guidewires are typically very narrow, having a diameter in their central, largest-diameter portion of about 0.01 to 0.02 inch. Thus, even though the proximal end of the guidewire may be squared off and not equipped with a point, at that narrow diameter the guidewire has a considerable capability of punching through a rubber glove and sometimes injuring the hand, if the surgeon is not careful in his operation. Of course any breach of a biological barrier as is provided by the rubber gloves is most undesirable, raising a risk of the spread of disease between the physician and the patient, especially in the situation of a vascular catheter guidewire, where blood can be present outside of the patient's body, and on the guidewire.

It is not a satisfactory solution to place an enlarged, proximal tip on the proximal end of the guidewire, because such an enlarged tip, while it would help to reduce accidental penetration of gloves by the guidewire proximal end, would interfere with the use of torquing devices. These devices are used for rotating the guidewire during the procedure of inserting the guidewire distal tip into a desired artery while controlling the guidewire from the proximal end thereof.

Guidewires such as that disclosed in Amplatz, U.S. Pat. No. 4,991,602 have blunt tips on the ends of tapered guidewire portions, but the tips are not substantially larger than the diameter of the main body of the guidewire. Furthermore, when one attempts to push such a guidewire from its end, either accidentally or purposely, such a wire tip is likely to collapse and kink with such pushing, which is of course undesirable.

By this invention, the above problems are addressed in such a manner as to provide an improved guidewire having a proximal end which cannot damage the surgeon's glove or hand as the wire is being manipulated, pushed, or the like. Nevertheless, the guidewire of this invention is capable of being attached at its proximal end to a currently available torquing device for rotation of the wire, to assist in the steering process as the wire is advanced.

DESCRIPTION OF THE INVENTION

By this invention a vascular catheter guidewire is provided, which comprises a length of wire having a proximal and a distal end. The wire defines a central portion between the ends having a first diameter range, preferably being substantially constant in diameter to about the nearest thousandth inch or so, and typically having a diameter of about 0.01 to 0.02 inch. However, variations of diameter are possible in various sections of the wire.

The distal end of the guidewire comprises a tip which is of greater flexibility than the wire of the central portion. This facilitates the steerability of the guidewire, as well as serving to protect against injury to blood vessels within the patient as the guidewire is advanced. The proximal end of the guidewire, by this invention, comprises a tip which is of greater flexibility than the wire of the central portion, but is also of less flexibility than the tip of the distal end.

The guidewire distal end and proximal end are each defined by a length of wire which is integral with the central wire portion, with these lengths of wire each having a range of diameters that are less than the first diameter range for the main body of the wire; i.e. typically no diameter of the lengths of wires of the tips is equal to any diameter of the wire of the central portion. Thus any coil present can be of about equal diameter to the main body. Also, the lengths of wire defining the tips are typically tapered down to minimum diameters at the proximal and distal ends of the guidewire.

The length of wire of the distal end tip has a length of at least three inches, and typically substantially more than three inches, extending out to fifteen inches and more in many cases.

The length of wire of the proximal end tip preferably has a length of no more than about two inches, which is sufficient to provide the end tip with enough flexibility to prevent puncturing of a rubber glove, at minimal cost.

Preferably, the proximal end tip carries a coil spring in surrounding relation. It is also typical for the distal end tip to be surrounded by a coil spring as well, in conventional manner.

Preferably, the proximal guidewire end defined by a blunt tip of greater diameter than the minimum wire diameter of the proximal guidewire end tip. The diameter of this blunt tip is preferably not substantially larger than the first diameter range of the central wire portion, so as not to interfere with conventional torquing devices which attach to the proximal guidewire end. Preferably, the length of the wire of the proximal tip is about three quarters to one and one half inches.

Thus, a guidewire has a proximal end in accordance with this invention which is as narrow as conventional guidewires, but which greatly decreases the risk that a guidewire at its proximal end can tear open a rubber glove or the like, or injure the fingers, as the guidewire is being manipulated.

DESCRIPTION OF SPECIFIC EMBODIMENTS

Figures 1, 2:
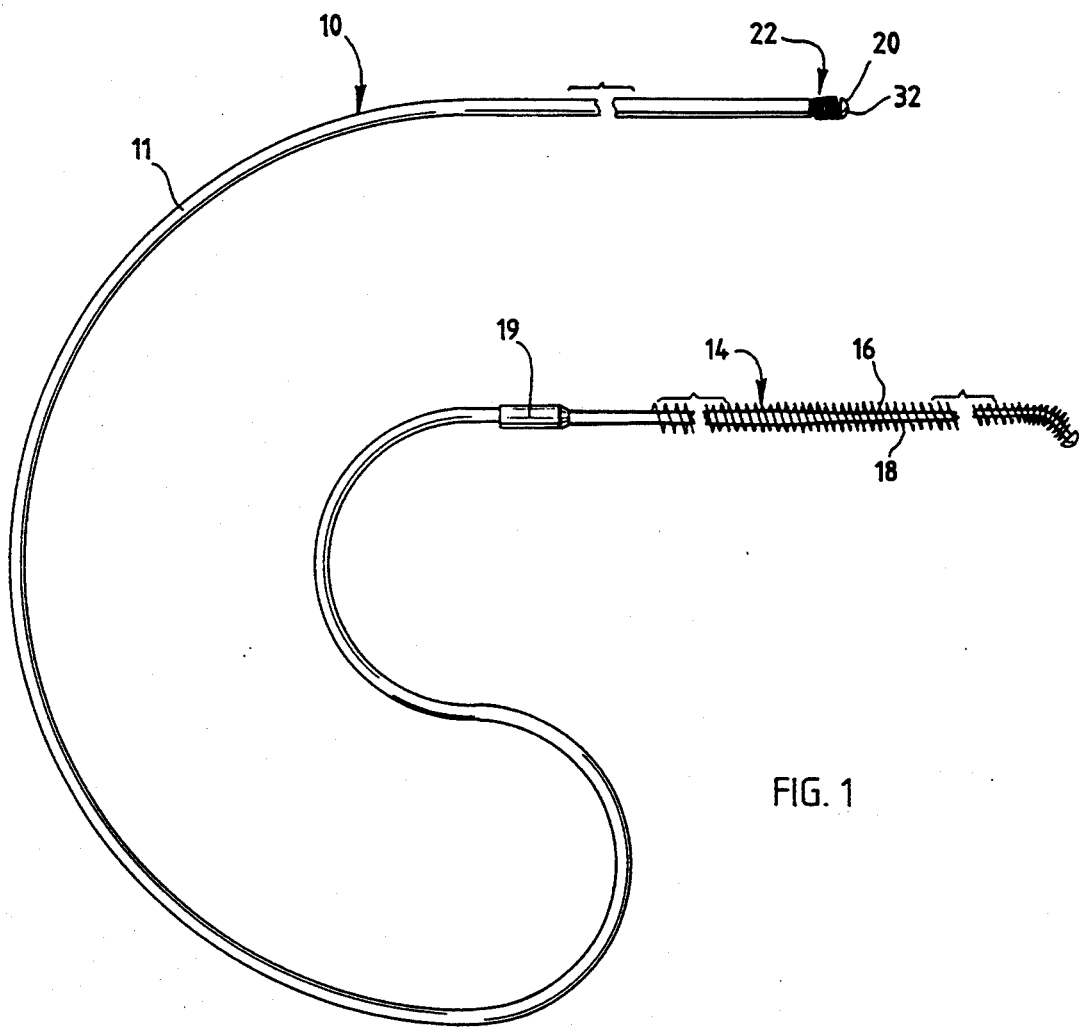
FIG. 1 is a plan view of a guidewire manufactured in accordance with this invention.
FIG. 2 is a fragmentary, enlarged, plan view of the proximal end of the guidewire of FIG. 1.

Referring to the drawing, guidewire 10 is shown in highly enlarged form for purposes of clear disclosure. Specifically, guidewire 10 may have a diameter 12 in its central portion of about 0.0125 to 0.0135 inch. This diameter may vary in a range of sizes in different versions of the guidewire, as is conventional for angioplasty and other surgical procedures.

Guidewire 10 defines a distal end 14, having a resilient, flexible tip which comprises a tapered down, thin portion 16 of the guidewire surrounded by a coil spring, in a manner similar to commercial embodiments of such guidewire tips, or in accordance with the disclosures of Box, et al. U.S. Pat. No. 4,846,186, which is incorporated herein by reference. Such a guidewire tip arrangement facilitates steering of the guidewire from the vicinity of the proximal guidewire end 20 by rotating the guidewire as it is advanced. It may have a curve near the distal end 14, or it may be straight.

Spring 18 of the distal end may be about 10½ or 11 inches long, for example, or similar dimensions in accordance with the disclosures of the Box, et al. patent, with the remaining dimensions of distal end 14 being similar to those disclosed in that patent. The entire guidewire may be about 71 inches long.

Polytetrafluoroethylene (PTFE) coating 19 is provided just adjacent to the tapered wire portion and slightly overlapping it. As a specific example, the diameter of the PTFE coating may be about 0.0143 inch.

In accordance with this invention, proximal end 20 of the guidewire is defined by a tip or tip portion 22, which is carried as an integral part of guidewire 10.

Guidewire proximal tip portion 22 comprises an integral section 28 of the guidewire which is of reduced diameter relative to the diameter of the main portion 11 of guidewire 10. Specifically, the reduced diameter guidewire portion 28 may be of a tapering diameter of about 0.006 to 0.008 inch, and may be surrounded by a coil spring 30. Reduced diameter portion 28 of the guidewire may be about 1 inch in length.

A hemispherical tip 32 may be plasma welded to the proximal end of reduced diameter guidewire portion 28 as shown, with tip 32 being of substantially equal diameter to the main portion 11 of the guidewire, so that it does not interfere with torquing devices that may be used on the guidewire.

The proximal end of coil spring 30 may be retained against the flat face of the hemispherical member 32. At the distal end of spring 30, spring 30 may be retained against annular shoulder 34, where the guidewire main portion 11 narrows down to reduced diameter guidewire portion 28. Alternatively, annular shoulder 34 may be tapered to form a conical section or some similar shape as is indicated at 34a, as an alternate structure to retain coil spring 30.

Spring 30 may be epoxied or soldered to the shaft 28 in the vicinity of annular surface 34 or 34a.

Being only an inch in length and being straight in its natural condition, proximal tip 22 is not especially suited as a distal end for enhancing the steerability of the guidewire 10. Rather, it is typically used exclusively as the proximal end, while distal end 14 provides the steerable tip. However, as one manipulates the guidewire and strikes the proximal end 20 thereof with the fingers, tip 22 tends to easily bend out of the way rather than resisting and tearing the rubber glove material. Despite that bending, the low diameter guidewire portion 28 is not subject to kinking because of the presence of the surrounding coil spring 30. Thus, it tends to snap back into straighter position, impelled in part by the coil spring after it has been deflected by striking a hand or the like.

However, while proximal tip 22 is more flexible than the central portion 11 of guidewire 10, it is typically stiffer than the distal tip 14 because it is shorter. Thus it is possible to exert a push on the guidewire from proximal end 20 without the immediate collapse of the tip 22. This facilitates procedures such as the pushing of coils through the vascular system of a patient to fill an aneurism. Thus the relatively increased stiffness of proximal tip 22 over distal tip 14 can be advantageous, even though proximal tip 22 has reduced stiffness when compared with the main body of the guidewire.

While the reduced diameter, proximal guidewire portion 28 is shown to be of a tapering version, a cylindrical guidewire portion 28 may also be used if desired.

Accordingly, a guidewire is provided which retains good pushability from its proximal end when that is needed, but which has a flexible enough proximal end to prevent tearing of rubber gloves, while at the same time still permitting the use of conventional torquing apparatus with the guidewire.

The above has been offered for illustrative purposes only, and is not intended to limit the scope of the invention of this application, which is as defined in the claims below.

That which is claimed is:

1. A vascular catheter guidewire which comprises a length of wire having a proximal and a distal end, said wire defining a central portion between the ends having a first diameter range, said distal end comprising a tip of greater flexibility than the wire of said central portion, said proximal end also comprising a tip of greater flexibility than the wire of said central portion, said distal end tip and proximal end tip being each defined by a length of wire integral with said central portion and each having a range of diameters that is less than the first diameter range, said distal end tip having a length of at least 3 inches, and the proximal end tip having a length of no more than about 2 inches, said distal end tip being of greater flexibility than said proximal end tip.

2. The guidewire of claim 1 in which said proximal end tip carries and is surrounded by a coil spring.

3. The guidewire of claim 1 in which said proximal guidewire end is defined by a blunt member of greater diameter than the proximal end wire diameter, said diameter of the blunt member being not substantially larger than said first diameter range.

4. The guidewire of claim 1 in which the length of wire of said proximal tip is ½ to 1½ inches in length.

5. A vascular catheter guidewire which comprises a length of wire having a proximal and a distal end, said wire defining a central portion between the ends having a first diameter range, said distal and proximal ends each comprising an end wire tip of greater flexibility than the wire of said central portion, said distal end tip and proximal end tip being each defined by a length of wire integral with said central portion and each having a range of diameters that is less than the first diameter range, said proximal end tip carrying a coil spring, being surrounded by said coil spring, said distal end tip being of greater flexibility than said proximal end tip, the distal end tip having a length of at least 3 inches, and the proximal end tip having a length of no more than about 2 inches.

6. The guidewire of claim 5 in which the length of wire of said proximal tip is ½ to 1½ inches in length.

7. The guidewire of claim 6 in which said proximal guidewire end is defined by a blunt member attached to said proximal end wire tip, said blunt member being of greater diameter than the proximal end wire at least in the vicinity of said attachment, said diameter of the blunt member being not substantially larger than said first diameter range.

8. The guidewire of claim 7 in which said distal end tip carries and is surrounded by a second coil spring.

9. The guidewire of claim 5 in which said distal end tip carries and is surrounded by a second coil spring.

10. A vascular catheter guidewire which comprises a length of wire having a proximal and a distal end, said wire defining a central portion between the ends having a first diameter range, said distal end comprising a tip of greater flexibility than the wire of said central portion, said proximal end also comprising a tip of greater flexibility than the wire of said central portion, said distal end tip and proximal end tip being each defined by a length of wire integral with said central portion and each having a range of diameters that is less than the first diameter range, each of said proximal end tip and distal end tip carrying a coil spring which abuts a transverse face of said guidewire at each end of said coil spring, to be retained thereby at both ends, said distal end tip having a length of at least three inches and the proximal end tip having a length of no more than about two inches.

11. The guidewire of claim 10 in which said proximal and distal guidewire ends each comprise a blunt member of greater diameter than the respective proximal and distal end wire diameters, the diameter of said blunt member being not substantially larger than said first diameter range.

12. The guidewire of claim 11 in which the length of wire of said proximal tip is one half to one and one half inches in length.

13. The guidewire of claim 12 in which said distal end tip is of greater flexibility than said proximal end tip.

14. The guidewire of claim 10 in which the length of wire of said proximal tip is one half to one and one half inches in length.

* * * * *